(12) United States Patent
Deuter

(10) Patent No.: US 7,507,371 B2
(45) Date of Patent: Mar. 24, 2009

(54) METHOD FOR DISINFECTING A CUVETTE COVER

(75) Inventor: Klaus Deuter, Unterschleissheim (DE)

(73) Assignee: LRE Medical GmbH, Munich (DE)

( * ) Notice: Subject to any disclaimer, the term of this patent is extended or adjusted under 35 U.S.C. 154(b) by 561 days.

(21) Appl. No.: 11/135,872

(22) Filed: May 24, 2005

(65) Prior Publication Data

US 2005/0265891 A1 Dec. 1, 2005

(30) Foreign Application Priority Data

May 25, 2004 (DE) .................. 10 2004 025 587

(51) Int. Cl.
*A61L 2/04* (2006.01)
(52) U.S. Cl. .............................. 422/28; 422/1; 422/292; 422/307

(58) Field of Classification Search ................... 422/28, 422/1, 292, 307
See application file for complete search history.

(56) References Cited

U.S. PATENT DOCUMENTS 6,209,591 B1 * 4/2001 Taggart .................... 141/89
6,414,274 B1 * 7/2002 Mahyari .................... 219/386

* cited by examiner

*Primary Examiner*—Sean E Conley
(74) *Attorney, Agent, or Firm*—McCormick, Paulding & Huber LLP

(57) ABSTRACT

The invention concerns a method and an apparatus for disinfecting a cuvette cover. The opening of a cuvette (14) containing a test fluid is temporarily covered while the cuvette is at a processing station. The surface of the cover facing the cuvette opening in the lifted condition of the cover is heated to a temperature suitable for the killing of microorganisms on the cover.

3 Claims, 2 Drawing Sheets

METHOD FOR DISINFECTING A CUVETTE COVER

CROSS REFERENCE TO RELATED APPLICATIONS

The priority of German Patent Application 10 2004 025 587.3 of May 25, 2004 is claimed, and the disclosure of the German Patent Application is incorporated by reference.

FIELD OF THE INVENTION

The invention concerns a method for disinfecting a cover by means of which the opening of a cuvette containing a test fluid is temporarily covered while the cuvette is at a processing station.

BACKGROUND OF THE INVENTION

The method according to the invention is designed for a known automatic machine in which a plurality of test fluids can be analyzed in sequence. These test fluids can contain microorganisms and usually are delivered to the automatic machine in cuvettes from which the automatic machine takes the test fluid with the help of a pipette in order to load them into the measuring chambers of so-called microtitration plates. The measuring chambers can be loaded with a nourishing solution and/or detection chemicals for certain microorganisms. Before the test fluid can be loaded into the microtitration plate, it must as the case may be, be preprocessed, for example, be homogenized or thinned. The homogenization can, for example, take place with the help of an ultrasonic mixer. However, the danger exists that an atomized spray of the test fluid can escape from the cuvette opening. Because of this, the cuvette cover must be closed at least during the homogenization process. With this the problem arises that the cover itself becomes dirty and with a change of cuvettes microorganisms can be transmitted from one cuvette to the following cuvette by the cover. Naturally this must be avoided under all circumstances.

One solution exists in that the cover surface is wiped off with each cuvette change. A wiping mechanism necessary for this is not only complicated but also does not solve the problem since the washing organ itself must also be disinfected in order to avoid a spreading of the microorganisms. With the use of disinfecting chemicals there exists the danger of a contamination of the test fluids and a damaging of the microorganisms contained in the fluids.

The invention has as its object the provision of a method by means of which the cover surface can be disinfected reliably in a simple way.

SUMMARY OF THE INVENTION

For the solution of the mentioned object in accordance with the invention it is proposed that the surface of the cover facing the cuvette opening in a lifted condition of the cover be heated to a temperature suitable for the killing of microorganisms on the cover.

The solution of the invention requires neither moving parts nor chemicals which could contaminate the test fluids. The temperature to which the cover surface is heated can be chosen to be so high that the microorganisms present on the cover surface are essentially burned.

An especially simple solution exists for example in that at least one layer of the cover which includes the surface to be heated is electrically conductive and in that for heating the surface an electrical current is conducted through the layer. Such a solution is simple to realize and reliable to control. The electric heating of the cover surface offers also the possibility of measuring the electrical resistance of the layer through which the current flows and from the measured value determining the temperature of the heated surface in order to have a control assuring that the microorganisms are actually reliably destroyed. Another possibility for the temperature determination exists in that the infrared radiation emitted from the heated surface is measured and from that measurement the temperature is determined.

The invention further concerns an apparatus for disinfecting a cover by means of which the opening of a test fluid containing cuvette is temporarily covered while the cuvette is in a processing station. According to the invention, the cover which is movable relative to the cuvette opening has associated with it a heating device for heating the surface of the cover facing the cuvette opening.

Preferably the cover includes a pressing element movable relative to the cuvette opening and a metal strip pressable by the pressing element onto the cuvette opening, which metal strip for example is part of a spring element which is biased toward a lifted position away from the cuvette opening.

BRIEF DESCRIPTION OF THE DRAWINGS

Further features and advantages of the invention will be apparent from the claims below as well as from the following description which in combination with the accompanying drawings explain the invention by way of an exemplary embodiment.

DESCRIPTION OF THE PREFERRED EMBODIMENTS

Figure 1:
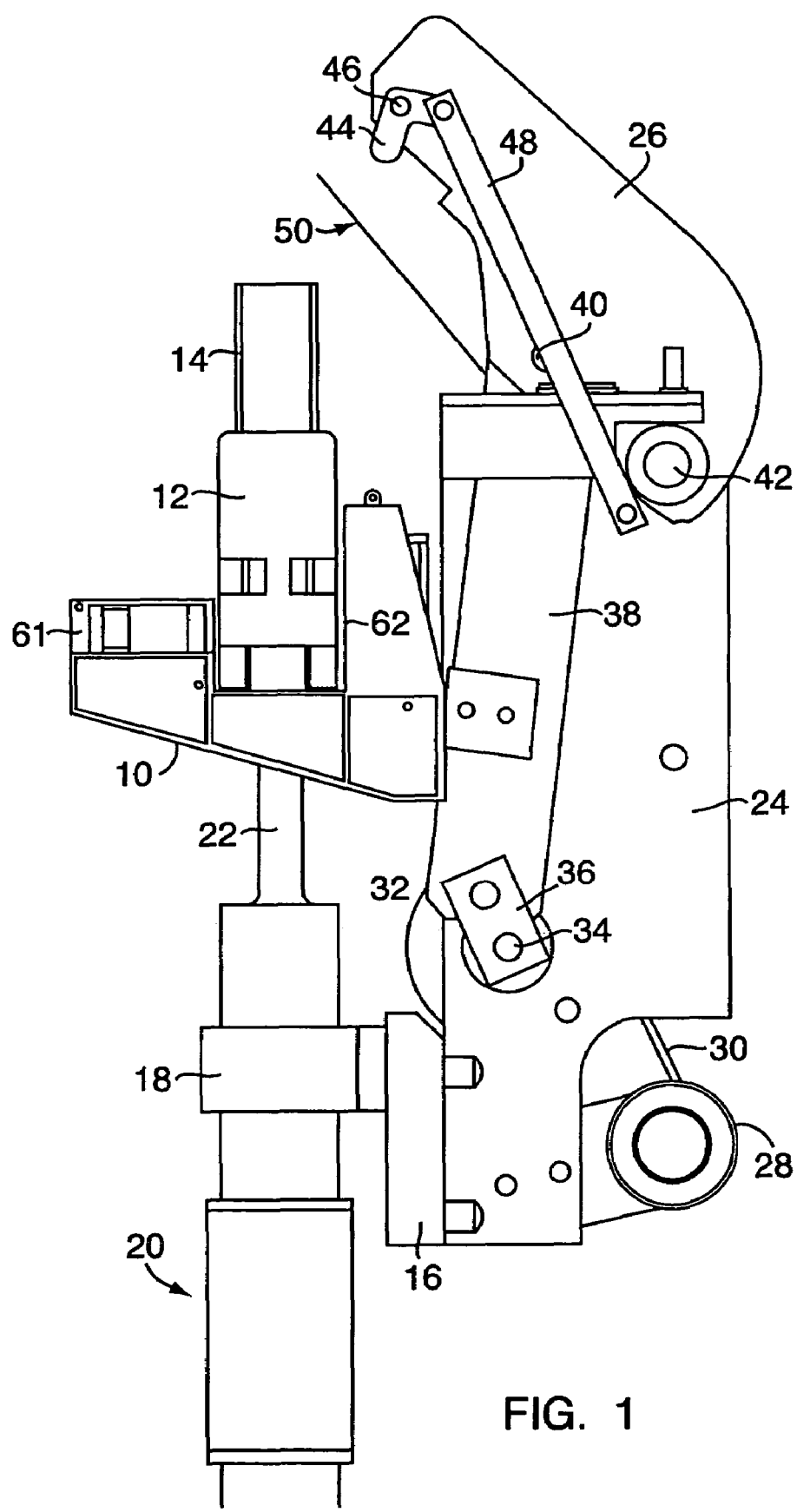
FIG. 1 is a partial schematic illustration of a mixing station for homogenizing a test fluid contained in a cuvette, wherein the cover for closing the cuvette opening is shown lifted from the cuvette.
Figures 2, 3:
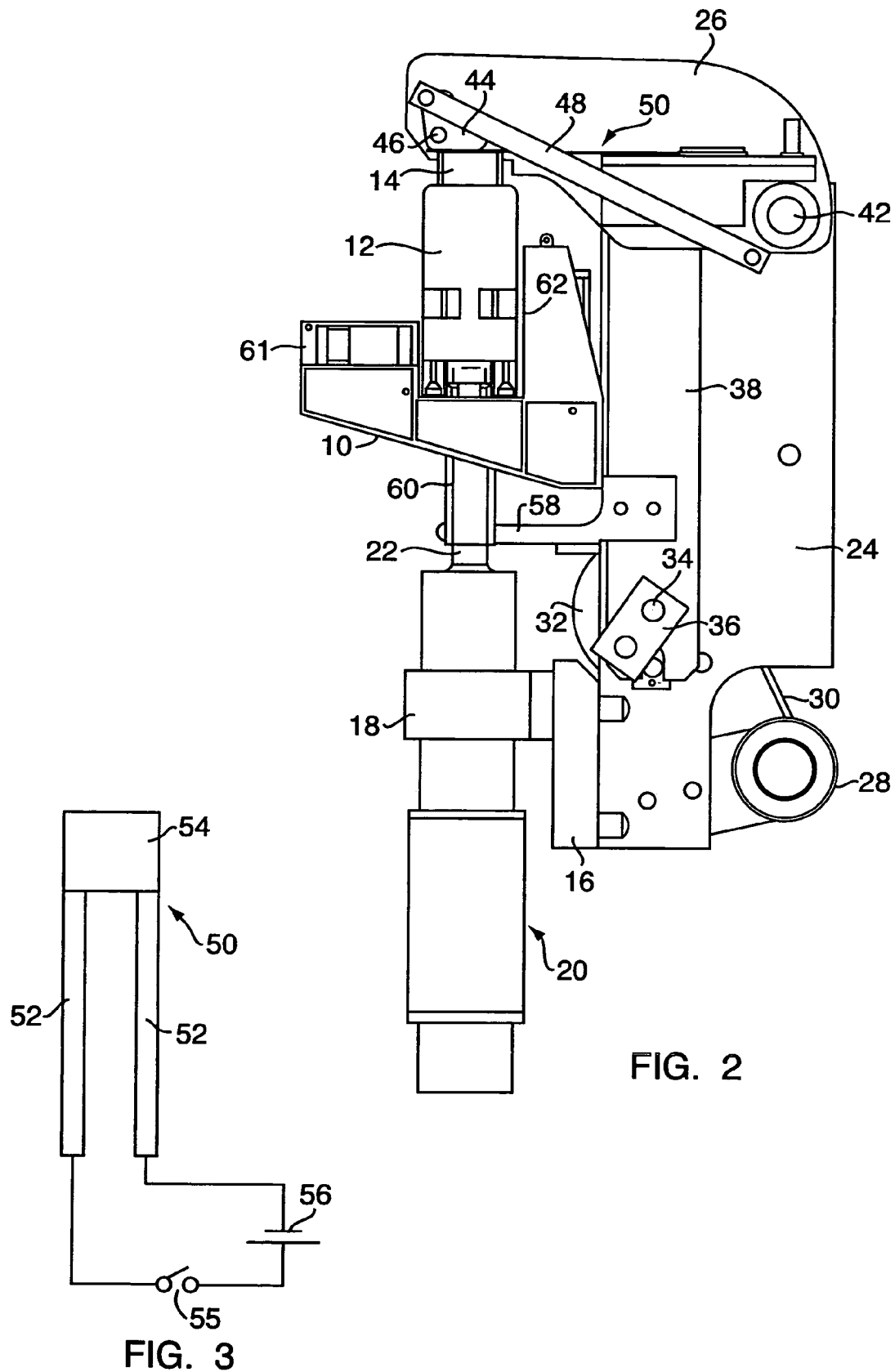
FIG. 2 is a figure corresponding to FIG. 1 wherein a cuvette is shown to be closed by the cover.
FIG. 3 is a schematic plan view of an electrically heatable leaf spring arrangement which forms a part of the cuvette cover.

The mixing apparatus shown in FIGS. 1 and 2 for homogenizing a test fluid in a cuvette is part of an automatic analyzing machine for analyzing test fluids. Seen in these figures is a guide rail (10) fixedly connected with the chassis of the non-illustrated automatic analyzing machine for a cuvette rack (12) which can receive a plurality of cuvettes (14), which cuvettes are arranged behind one another in the viewing direction of FIGS. 1 and 2. While in this cuvette rack the cuvettes (14) are moved through the several processing stations of the automatic analyzing machine.

On a carrier (16), likewise rigidly fixed to the chassis of the automatic analyzing machine, there is arranged below the guide rail (10) by means of a bracket (18) an ultrasonic mixing head (20) whose sonotrode (22) through a corresponding opening in the guide rail (10) and in the cuvette rack (12) comes in contact with the bottom of each cuvette (14) brought to the mixing position to introduce ultrasonic energy through the cuvette bottom into the test fluid in the cuvette (14).

A stand (24) is further fixed to the carrier (16) on which a pressing arm (26) is movable between a lifted open position illustrated in FIG. 1 and a lowered closed position illustrated in FIG. 2. The movement mechanism includes a motor (28)

fastened to the lower end of the stand which motor by means of a drive belt (30) drives a belt pulley (32) supported in the stand (24). The shaft (34) of said belt pulley is non-rotatably fixed to one end of a crank arm (36) whose other end is pivotably connected with the lower end of a double link (38). The upper end of the double link (38) is pivotably linked to the pressing arm (28) for movement about an axis of (40), in order to move the pressing arm about it's pivot axis (42) between the positions illustrated in FIGS. 1 and 2.

An angularly shaped pressing element (44) is linked to the pressing arm near the free end of the pressing arm for movement about an axis (46), which pressing element is moved by a lever (48) pivotably connected at one end to the stand (24) and at its other end to the pressing element (44) so as to move the pressing element (26) between the positions illustrated in the FIGS. 1 and 2 upon pivoting movement of the pressing arm (26). A spring element (50) is fastened to the upper end of the stand (24) and forms a part of the cover for the cuvette opening. The spring element (50) is illustrated in more detail in FIG. 3 and includes two strip shaped leaf spring arms (52) which at their one ends are connected together by a thin metallic heating foil (54) and which at their other ends are connected to the stand by rivets or screws in an electrical isolating manner. These two ends are connected through a switch (55) to a current source (56). The leaf spring arms (52) are so biased that the spring-element (50) in its unloaded condition takes on the position illustrated in FIG. 1. With a lowering of the pressing arm (26) the pressing element (44) takes along with it the spring element (50) and presses its metal foil (54) against the opening of the cuvette (12) so that the cuvette becomes closed, as is illustrated in FIG. 2. At the same time the pressing arm serves in its closed position to provide a good contact between the cuvette (14) and the sonotrode (22) of the ultrasonic mixer (20). The arrangement can be so designed that the switch (55) is controlled by the positioning movement of the pressing arm (26).

To free the metal foil (54) from possible microorganisms after the mixing, the foil (54) is heated by connection with the voltage source (56), so that microorganisms possibly clinging to the foil are destroyed. As seen in FIG. 1 the spring element (50) and especially the foil (54) are lifted entirely free from the pressing element (44). Because of its small mass, the foil (54) can quickly and with little consumption of energy be heated to a relatively high temperature, and after turning off the voltage source it can therefore also likewise be again quickly cooled. The small thermal inertia of the element (54) makes possible a high repetition rate in the processing of the cuvettes.

As is further seen in FIGS. 1 and 2, the doublelink (38) is connected with a fork arm (58) which by means of a sleeve (60) surrounding the sonotrode (22) can lift the cuvette (12) from the position illustrated in FIG. 2 to the position illustrated in FIG. 1 when the pressing arm (26) is moved to its open position. This provides the possibility of optically measuring the cuvette (14) at different elevations of the cuvette, preferably with the help of an optical measuring device including a light emitter (61) and a light receiver (62).

The invention claimed is:

1. A method for disinfecting a cover of an opening of a cuvette containing a test fluid while the cuvette is located at a processing station, the method comprising heating a surface of the cover facing the cuvette opening to a temperature which is suitable for the killing of microorganisms on the cover while the cover is in a raised position relative to the opening. wherein at least one layer of the surface of the cover to be heated is electrically conductive, and the step of heating further comprises conducting an electrical current through the conductive layer for heating the surface.

2. The method according to claim 1 further comprising the step of measuring electrical resistance value of the conductive layer, the temperature of the surface to be heated being determined from the measured value.

3. The method according to claim 1 further comprising the step of determining the temperature of the surface to be heated from infrared rays emitted therefrom.

* * * * *

UNITED STATES PATENT AND TRADEMARK OFFICE
CERTIFICATE OF CORRECTION

| | | |
|---|---|---|
| PATENT NO. | : 7,507,371 B2 | Page 1 of 1 |
| APPLICATION NO. | : 11/135872 | |
| DATED | : March 24, 2009 | |
| INVENTOR(S) | : Klaus Deuter | |

It is certified that error appears in the above-identified patent and that said Letters Patent is hereby corrected as shown below:

Column 4, line 26, after the word "opening" please delete "." and insert --,--.
Column 4, line 32, please insert --an-- after the word "measuring".

Signed and Sealed this

Twelfth Day of May, 2009

JOHN DOLL
*Acting Director of the United States Patent and Trademark Office*